United States Patent
Bailey et al.

(10) Patent No.: US 9,271,759 B2
(45) Date of Patent: Mar. 1, 2016

(54) PEDICLE SCREW ASSEMBLY WITH LOCKING CAP

(71) Applicant: The Institute of Musculoskeletal Science and Education, Radnor, PA (US)

(72) Inventors: Gregory Bailey, State College, PA (US); Joel Torretti, State College, PA (US)

(73) Assignee: Institute of Musculoskeletal Science and Education, Ltd., Wayne, PA (US)

( * ) Notice: Subject to any disclaimer, the term of this patent is extended or adjusted under 35 U.S.C. 154(b) by 0 days.

(21) Appl. No.: 13/789,972

(22) Filed: Mar. 8, 2013

(65) Prior Publication Data

US 2013/0253589 A1    Sep. 26, 2013

Related U.S. Application Data

(60) Provisional application No. 61/609,076, filed on Mar. 9, 2012.

(51) Int. Cl.
*A61B 17/88* (2006.01)
*A61B 17/70* (2006.01)

(52) U.S. Cl.
CPC ............. *A61B 17/7032* (2013.01); *A61B 17/88* (2013.01)

(58) Field of Classification Search
CPC .......... A61B 17/7032; A61B 17/7037; A61B 17/7035; A61B 17/7049
USPC .......... 606/264–270, 272; 411/377, 396, 517, 411/530
See application file for complete search history.

(56) References Cited

U.S. PATENT DOCUMENTS

| | | | |
|---|---|---|---|
| 5,443,467 A | 8/1995 | Biedermann | |
| 5,667,508 A | 9/1997 | Errico | |
| 5,989,254 A | 11/1999 | Katz | |
| 6,022,350 A * | 2/2000 | Ganem | 606/272 |
| 6,113,601 A | 9/2000 | Tatar | |
| 6,371,957 B1 * | 4/2002 | Amrein et al. | 606/272 |
| 6,565,565 B1 | 5/2003 | Yuan | |
| 6,645,207 B2 | 11/2003 | Dixon | |
| 6,652,526 B1 | 11/2003 | Arafiles | |
| 6,656,181 B2 | 12/2003 | Dixon | |
| 6,755,829 B1 | 6/2004 | Bono | |
| 6,786,903 B2 | 9/2004 | Lin | |
| 6,896,677 B1 | 5/2005 | Lin | |
| 6,986,771 B2 | 1/2006 | Paul | |
| 6,989,011 B2 | 1/2006 | Paul | |
| 7,081,117 B2 | 7/2006 | Bono | |
| 7,125,426 B2 | 10/2006 | Moumene | |
| 7,141,051 B2 | 11/2006 | Janowski | |
| 7,264,621 B2 | 9/2007 | Coates | |
| 7,338,491 B2 | 3/2008 | Baker | |

(Continued)

*Primary Examiner* — Mary Hoffman
*Assistant Examiner* — Tara R Carter
(74) *Attorney, Agent, or Firm* — Pabst Patent Group LLP

(57) ABSTRACT

A locking pedicle screw assembly has been designed which avoids misalignment and locks into place once the cap is fully threaded into the tulip, avoiding over tightening or stripping of the threads. The locking cap includes a retaining or locking ring, positioned either at the bottom of the cap so that it locks into a groove at the bottom of the threads in the tulip or at the top of the threads in the cap, locking into a groove at the top of the tulip when the cap is fully seated. In one embodiment, an audible signal is generated when the cap locks. In another embodiment, the cap is secured to a swiveling saddle that locks the rod into place as the screw cap is tightening, but does not interfere with the locking mechanism.

12 Claims, 5 Drawing Sheets

(56) References Cited

U.S. PATENT DOCUMENTS

| | | |
|---|---|---|
| 7,503,924 B2 | 3/2009 | Lee |
| 7,559,942 B2 | 7/2009 | Paul |
| 7,604,656 B2 | 10/2009 | Shluzas |
| 7,608,095 B2 | 10/2009 | Yuan |
| 7,678,137 B2 | 3/2010 | Butler |
| 7,731,749 B2 | 6/2010 | Biedermann |
| 7,766,946 B2 | 8/2010 | Bailly |
| 7,776,067 B2 | 8/2010 | Jackson |
| 7,780,703 B2 | 8/2010 | Yuan |
| 7,811,310 B2 | 10/2010 | Baker |
| 7,819,901 B2 | 10/2010 | Yuan |
| 7,833,252 B2 | 11/2010 | Justis |
| 7,842,073 B2 | 11/2010 | Richelsoph |
| 7,867,257 B2 | 1/2011 | Na |
| 7,909,856 B2 | 3/2011 | Yuan |
| 7,942,910 B2 | 5/2011 | Doubler |
| 7,942,911 B2 | 5/2011 | Doubler |
| 7,951,173 B2 | 5/2011 | Hammill |
| 7,951,174 B2 | 5/2011 | Kwak |
| 7,955,359 B2 | 6/2011 | Matthis |
| 7,955,363 B2 | 6/2011 | Richelsoph |
| 7,967,850 B2 | 6/2011 | Jackson |
| 8,012,186 B2 | 9/2011 | Pham |
| 8,034,086 B2 | 10/2011 | Iott |
| 8,038,702 B2 | 10/2011 | Yuan |
| 8,048,124 B2 | 11/2011 | Chin |
| 8,057,519 B2 | 11/2011 | Justis |
| 8,062,340 B2 | 11/2011 | Berrevoets |
| 8,075,590 B2 | 12/2011 | Janowski |
| 8,075,599 B2 | 12/2011 | Johnson |
| 8,075,603 B2 | 12/2011 | Hammill, Sr. |
| 2,002,957 A1 | 2/2012 | Suh |
| 8,162,989 B2 | 4/2012 | Khalili |
| 8,167,793 B2 | 5/2012 | Scott |
| 8,241,341 B2 | 8/2012 | Walker |
| 2002/0120272 A1 | 8/2002 | Yuan |
| 2002/0143341 A1* | 10/2002 | Biedermann et al. ............ 606/73 |
| 2003/0004511 A1 | 1/2003 | Ferree |
| 2003/0125742 A1 | 7/2003 | Yuan |
| 2003/0187433 A1 | 10/2003 | Lin |
| 2003/0187434 A1 | 10/2003 | Lin |
| 2004/0153068 A1 | 8/2004 | Janowski |
| 2004/0186473 A1* | 9/2004 | Cournoyer et al. ............. 606/61 |
| 2004/0236330 A1 | 11/2004 | Purcell |
| 2004/0260283 A1* | 12/2004 | Wu et al. ......................... 606/61 |
| 2005/0033296 A1 | 2/2005 | Bono |
| 2005/0131410 A1 | 6/2005 | Lin |
| 2005/0177154 A1 | 8/2005 | Moumene |
| 2005/0187548 A1 | 8/2005 | Butler |
| 2005/0228385 A1* | 10/2005 | Iott et al. ......................... 606/61 |
| 2005/0283157 A1 | 12/2005 | Coates |
| 2005/0288671 A1 | 12/2005 | Yuan |
| 2006/0004357 A1 | 1/2006 | Lee |
| 2006/0025767 A1 | 2/2006 | Khalili |
| 2006/0129149 A1 | 6/2006 | Iott |
| 2006/0149241 A1 | 7/2006 | Richelsoph |
| 2006/0161152 A1 | 7/2006 | Ensign |
| 2006/0217716 A1 | 9/2006 | Baker |
| 2006/0247636 A1 | 11/2006 | Yuan |
| 2006/0264933 A1 | 11/2006 | Baker |
| 2006/0276789 A1 | 12/2006 | Jackson |
| 2006/0293665 A1 | 12/2006 | Shluzas |
| 2007/0055235 A1 | 3/2007 | Janowski |
| 2007/0055241 A1 | 3/2007 | Matthis |
| 2007/0088357 A1 | 4/2007 | Johnson |
| 2007/0161999 A1* | 7/2007 | Biedermann et al. ........... 606/61 |
| 2007/0213731 A1 | 9/2007 | Prusmack |
| 2007/0233078 A1 | 10/2007 | Justis |
| 2007/0233080 A1 | 10/2007 | Na |
| 2007/0270813 A1 | 11/2007 | Garamszegi |
| 2007/0282341 A1 | 12/2007 | Hes |
| 2008/0015580 A1 | 1/2008 | Chao |
| 2008/0015584 A1 | 1/2008 | Richelsoph |
| 2008/0015597 A1 | 1/2008 | Whipple |
| 2008/0045953 A1* | 2/2008 | Garamszegi ..................... 606/61 |
| 2008/0045955 A1 | 2/2008 | Berrevoets |
| 2008/0147121 A1 | 6/2008 | Justis |
| 2008/0177322 A1 | 7/2008 | Davis |
| 2008/0177332 A1 | 7/2008 | Reiley |
| 2008/0183215 A1 | 7/2008 | Altarac |
| 2008/0195159 A1 | 8/2008 | Kloss |
| 2008/0200956 A1 | 8/2008 | Beckwith |
| 2008/0287998 A1 | 11/2008 | Doubler |
| 2008/0294203 A1 | 11/2008 | Kovach |
| 2009/0030457 A1 | 1/2009 | Janowski |
| 2009/0036929 A1 | 2/2009 | Reglos |
| 2009/0062866 A1 | 3/2009 | Jackson |
| 2009/0082819 A1 | 3/2009 | Blain |
| 2009/0306720 A1 | 12/2009 | Doubler |
| 2009/0318974 A1 | 12/2009 | Yuan |
| 2010/0004694 A1 | 1/2010 | Little |
| 2010/0063552 A1 | 3/2010 | Chin |
| 2010/0094352 A1 | 4/2010 | Iott |
| 2010/0137920 A1 | 6/2010 | Hammill |
| 2010/0198273 A1 | 8/2010 | Kwak |
| 2010/0268280 A1 | 10/2010 | Yuan |
| 2010/0312279 A1 | 12/2010 | Gephart |
| 2011/0009911 A1 | 1/2011 | Hammill |
| 2011/0106166 A1 | 5/2011 | Keyer |
| 2011/0125196 A1 | 5/2011 | Quevedo |
| 2011/0144701 A1 | 6/2011 | Altarac |
| 2011/0160779 A1 | 6/2011 | Schlaepfer |
| 2011/0196431 A1 | 8/2011 | Chao |
| 2011/0208250 A1 | 8/2011 | Kwak |
| 2011/0218579 A1 | 9/2011 | Jackson |
| 2011/0270325 A1 | 11/2011 | Keyer |
| 2011/0307016 A1 | 12/2011 | Reglos |
| 2012/0029569 A1 | 2/2012 | Iott |
| 2012/0265258 A1 | 10/2012 | Garvey |
| 2012/0303064 A1 | 11/2012 | Walker |

* cited by examiner

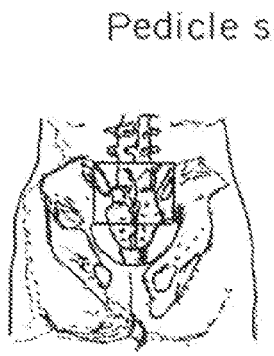
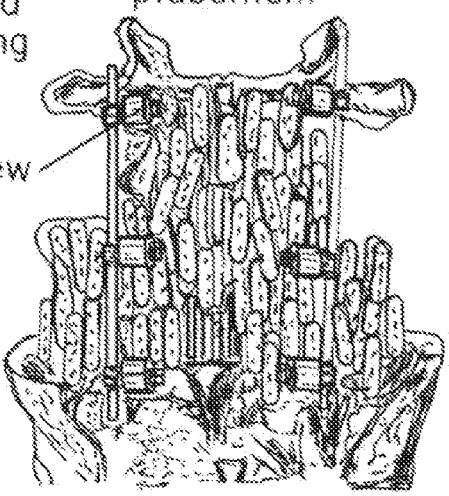
Pedicle screw
Pedicle screws are added to give strength to fusing vertebrae
Pedicle screw
Pedicle screw placement
FIG. 1A
PRIOR ART
FIG. 1B
PRIOR ART
*ADAM.
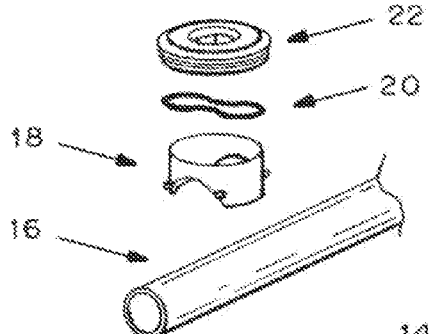
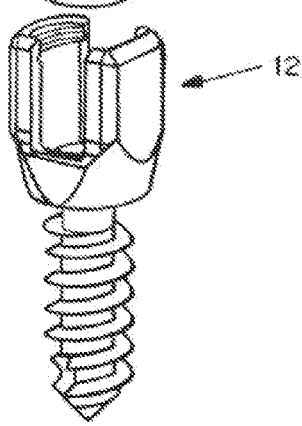
FIG. 2

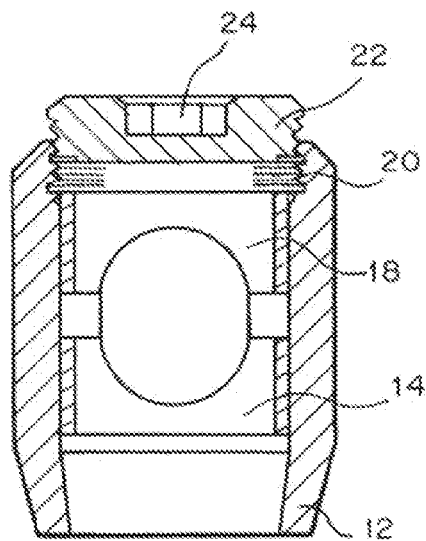
FIG. 3A
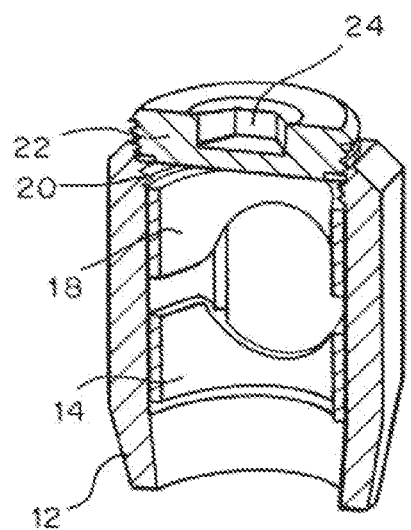
FIG. 3B
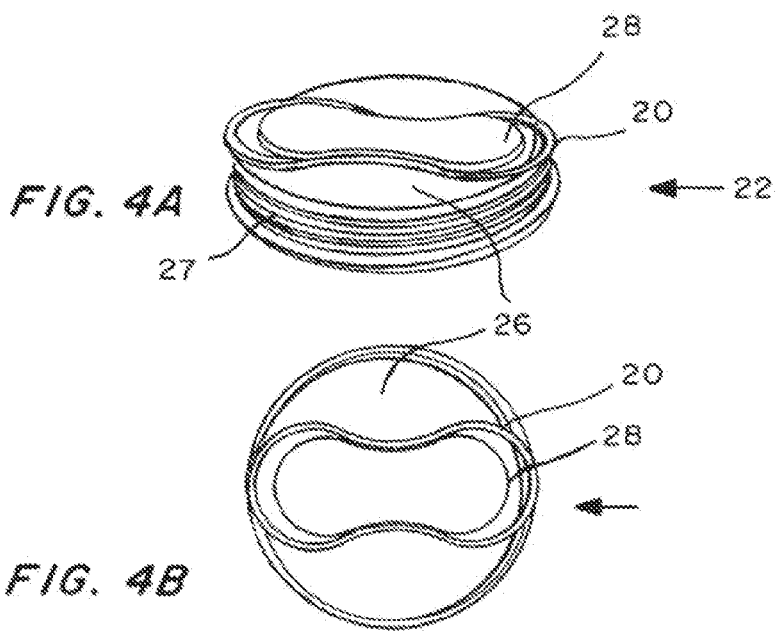
FIG. 4A
FIG. 4B

PEDICLE SCREW ASSEMBLY WITH LOCKING CAP

CROSS-REFERENCE TO RELATED APPLICATION

This application claims priority to U.S. Ser. No. 61/609,076, entitled "Pedicle Screw Assembly with Locking Cap" to Gregory Bailey and Joel Torretti, filed Mar. 9, 2012. The disclosure of which is incorporated herein by reference.

FIELD OF THE INVENTION

This invention relates to pedicle screws with locking caps to facilitate placement of rods during spinal fusion surgery.

BACKGROUND OF THE INVENTION

Fusion plates are used to immobilize and fuse adjacent spinal vertebrae following a discectomy (spinal disc removal) or for immobilizing the area surrounding a corpectomy (removal of an entire vertebral body). These procedures create a gap in the spine from the removed disc or vertebral body. The gap typically is closed by inserting a bone graft, usually from a cadaver. The adjacent vertebrae surrounding the discectomy or corpectomy site are then immobilized by attaching a fusion plate, usually on the anterior side of the spine, so that the vertebrae fuse to the bone graft, forming an entire fused section of the spine. Fusing of vertebrae to the bone graft requires that the vertebrae remain immobile.

The term "fusion" means achieving a rigid bone union. When metallic internal fixation devices were first introduced in the 1950s it soon became evident that the stress factors directed to this instrumentation by the human body turned out to be much greater than anticipated, leading to a quest for structurally stronger instrumentation rather than a quest for more functional and physiologic stabilizations.

Devices such as the Luqué ring allowed better fixation than its predecessors but the laminar wires needed to attach the ring to the lamina were unwieldy and, if the system was removed at a late date, the fixating wires, (which had an unfortunate tendency to erode through the adjacent dura mater), could create serious cerebro-spinal fluid leakage problems. Ring implants fell into disuse with spine surgeons when their attention became focused on pedicle screw fixation systems in the 1960s. Boucher, in 1959, has been credited as being the first to use pedicle screws but it was Roy-Camille, in the late 1970s, who was the first to use screws and hooks and connecting them with rods or plates. In 1983 Arthur Steffee patented the VSP spinal fixation system.

The early pedicle screw fixation systems utilized rather thick rods to support the screws. Not only were the rods difficult to bend at surgery but they tended to exert significant adverse stress on the screws and adjacent spinal segments. Complications involving nerve compression or injury associated with the placement of pedicle screws still occur in approximately 8-15% of cases. With heavy rods and large screws these problems tended to be increased. Initially, fractures of both pedicles and screws were fairly common.

An important advance in spinal fusion systems was the replacement of heavy plates with rods, particularly those allowing some degree of flexibility. Front and back (360° fusion) became possible, as well as anterior interbody femoral ring allografts placed at multiple levels. The front and back approach was the first type of fusion capable of producing consistently solid and rigid spine stabilization, even among patients who were smokers when multi-level rigid stabilization was considered desirable Today, there are many different types of metal devices used to perform a lumbar fusion. These devices connect two or more vertebrae together, hold them in the correct position, and keep them from moving until they have a chance to grow together, or fuse. This is not an easy task. The vertebrae are small, so there is not much room to put in the screws, plates, or metal rods that surgeons typically use to connect bones. Another problem is that many nerves get in the way of putting screws into the vertebral body. Finally, there is a great deal of stress across the lumbar spine when standing upright or even sitting. Finding a metal device that is able to hold the bones together can be difficult.

Most of the current devices that surgeons favor use metal screws that are placed through the small tube of bone, called the pedicle, and into the vertebral body. These screws are attached to metal plates or metal rods that are bolted together in the back of the spine. This combination of hardware creates a solid "brace" that holds the vertebrae in place. These devices are intended to stop movement from occurring between the vertebrae that are being fused, allowing a solid fusion to occur. These metal devices give more stability to the fusion site and allow the patient to be out of bed much sooner.

The best applications of rigid pedicle screw and rod fixation systems have been in cases of post-traumatic spine instability, where the adjacent segments are basically normal. For patients with advanced scoliosis or deformity which can result in progressive pulmonary or neurologic impairment, or in the management of spinal trauma, pedicle screw systems can be life-saving.

Pedicle screws may be titanium or stainless steel construction. Screw design differs as well. For example there are:

Polyaxial screws, which allow the head to rotate and lock onto the rod at any angle, which is important for ease of insertion.

Monoaxial screws provide more rigidity and are important for deformity correction.

A tulip head allows for less rod bending since the head can angle to engage the rod.

Cannulated screws provide a central canal for placement over a K-wire during a percutaneous application.

Fenestrated screws are designed with multiple holes allowing for bony in-growth and/or influx of polymethylmethacrylate.

Vertebral stabilization systems containing both polyaxial pedicle screws and variations of vertebral hooks for effecting temporary vertebral fixation for spinal fusion procedures are currently available. These spinal systems are manufactured by large medical device companies such as Zimmer (ST360 Spinal Fixation System), Medtronic Sofamor Danek (CD Horizon Legacy System), DePuy Spine (of Johnson & Johnson) Fixation Systems, and Synthes (Click'X Spine System).

For at least the reasons discussed above, even rods and pedicle screws can be difficult to install, with small spaces, degenerate bone due to osteoporosis or cancer, and misaligned vertebrae.

It is therefore an object of the present invention to provide pedicle screws that are easier to install into the pedicles and to use to secure the spinal fixation system.

It is a further object of the invention to provide an improved method for securing a rod during spinal fusion surgery.

SUMMARY OF THE INVENTION

A locking pedicle screw assembly has been designed which avoids misalignment and locks into place once the cap is fully threaded into the tulip, avoiding over tightening or stripping of the threads. The locking cap includes a retaining or locking ring, positioned either at the bottom of the cap so that it locks into a groove at the bottom of the threads in the tulip or at the top of the threads in the cap, locking into a groove at the top of the tulip when the cap is fully seated. In one embodiment, an audible signal is generated when the cap locks. In another embodiment, the cap is secured to a swiveling saddle that locks the rod into place as the screw cap is tightening, but does not interfere with the locking mechanism.

BRIEF DESCRIPTION OF THE DRAWINGS

FIGS. 1A and 1B are views of the prior art pedicle screw-rod stabilization system for spinal fusion. FIG. 1A is a perspective view of the spine into which the device is implanted. FIG. 1B is a cross-sectional expanded view of the screws and rods in place.

FIG. 2 is an expanded view of the locking cap pedicle screw.

FIGS. 3A and 3B are cross-sectional views of the tulip showing the locking cap and retaining ring.

FIGS. 4A and 4B are perspective views of the locking cap with the retaining ring on the bottom of the locking cap.

DETAILED DESCRIPTION OF THE INVENTION

Figures 5A, 5B:
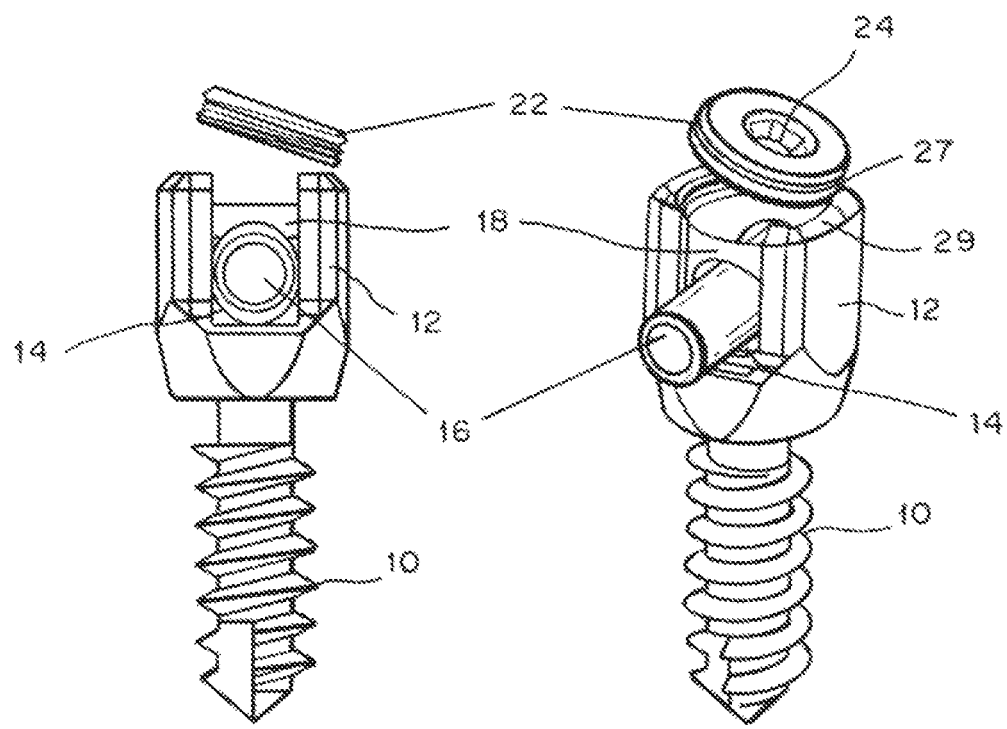
FIGS. 5A and 5B are perspective views of the locking cap-tulip-bone screw assembly showing how an initial misalignment (FIG. 5A) can be corrected by rotation of the locking cap until it is clicked into place in the first groove.

A locking pedicle screw has been designed to facilitate proper placement when securing the rods during a spinal fusion. A spinal fusion is depicted in FIGS. 1A and 1B, showing a prior art pedicle screw-rod stabilization system for spinal fusion.

I. Locking Pedicle Screw Caps

FIG. 2 is an expanded view of the locking cap pedicle screw assembly. A bone screw 10 is secured to a tulip 12 for placement of a spinal fusion rod 16. A bottom saddle 14 is positioned in the tulip 12 prior to placement of the rod 16. An upper saddle 18 is then placed over the rod 16 and the locking cap 22 and retaining ring 20 used to secure the rod 16 within the tulip 12.

FIGS. 3A and 3B are cross-sectional views of the tulip showing the locking cap 22 and retaining ring 20 positioned within the tulip 12. The cap 22 is secured using a hex-screwdriver inserted into hole 24, turning the threads 27 of the locking cap 22 into the threads 29 of the tulip 12. The cap 22 is locked into place by retaining ring 20, as shown in FIGS. 4A and 4B.

FIGS. 4A and 4B are perspective views of the bottom 26 of the locking cap 22 with the retaining ring 20 attached to protrusions 28 on the bottom of the locking cap 22.

FIGS. 5A and 5B are perspective views of the locking cap-tulip-bone screw assembly showing how an initial misalignment (FIG. 5A) can be corrected by rotation of the locking cap 22 until it is clicked into place in the first groove of threads 29 in tulip 12.

Figure 6A:
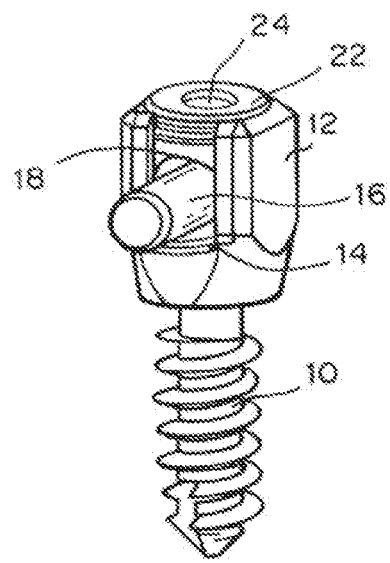
FIGS. 6A and 6B are perspective views of the locking cap-tulip-bone screw assembly showing the locking cap positioned for tightening using a hex-screwdriver (FIG. 6A) and tightened (FIG. 6B).
Figure 6B:
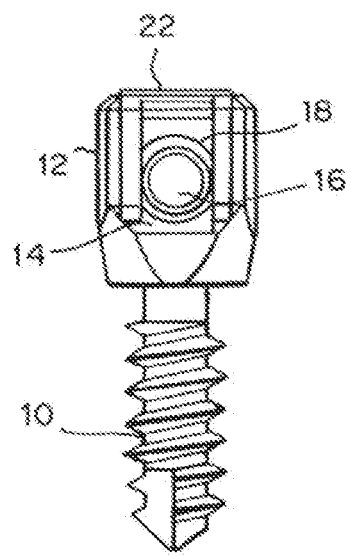

FIGS. 6A and 6B are perspective views of the locking cap-tulip-bone screw assembly showing the locking cap 22 positioned in the threads 29 for tightening using a hex-screwdriver (FIG. 6A) and after tightening (FIG. 6B).

Figure 7A:
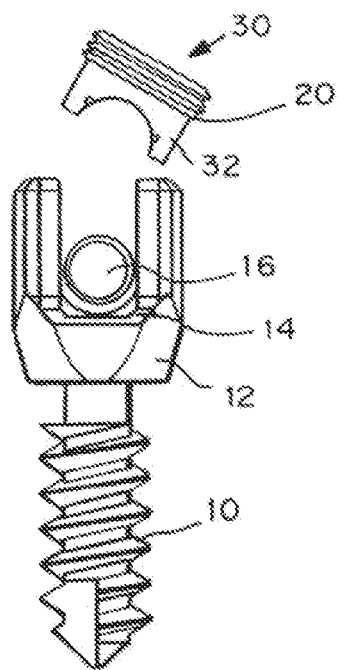
FIGS. 7A and 7B are perspective views of the locking cap-tulip-bone screw assembly with a modified locking cap-swiveling top saddle single piece with the retaining ring positioned at the top of the threads.
Figure 7B:
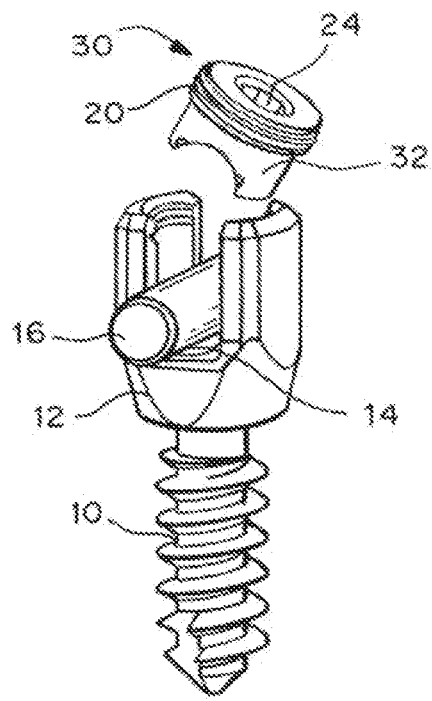

FIGS. 7A and 7B are perspective views of the locking cap-tulip-bone screw assembly with a modified locking cap-swiveling top saddle single piece 30 with the retaining ring 20 positioned at the top of the threads 27 on the cap 30. The saddle 32 swivels on the locking cap 30 so that it remains in place, securing rod 16 while the cap 30 is screwed into the tulip 12.

Figures 8A, 8B:
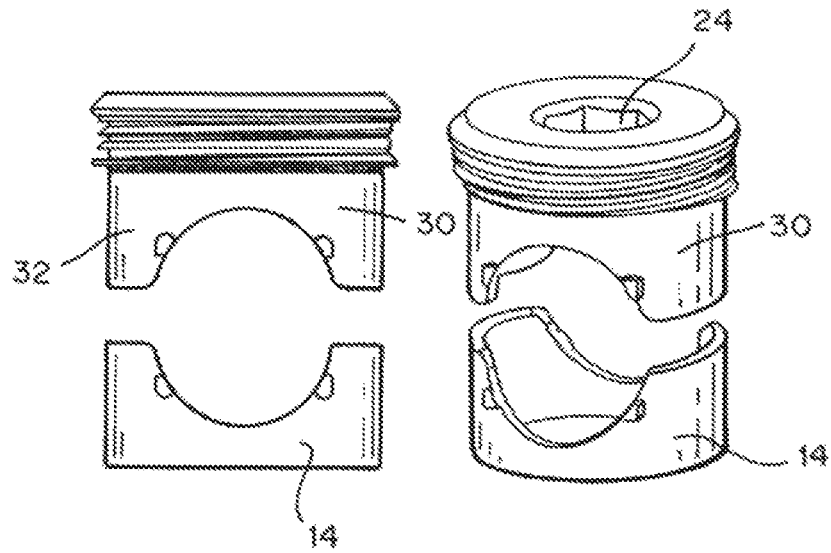
FIGS. 8A and 8B are a plan (FIG. 8A) and perspective view (FIG. 8B) of the modified locking cap-swiveling top saddle single piece with the retaining ring positioned at the top of the threads, in combination with a lower saddle for better retention of the rods.

FIGS. 8A and 8B are a plan (FIG. 8A) and perspective view (FIG. 8B) of the modified locking cap-swiveling top saddle single piece 32 with the retaining ring 20 positioned at the top of the threads 29, in combination with a lower saddle 14 for better retention of the rod 16.

Figure 9A:
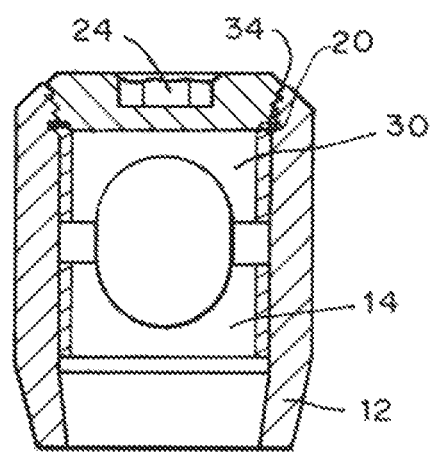
FIGS. 9A and 9B are cross-sectional views of the locking cap-tulip assembly including a groove in the bottom of the threads in the tulip, which produces an audible sound when the cap is completely threaded into the tulip.
Figure 9B:
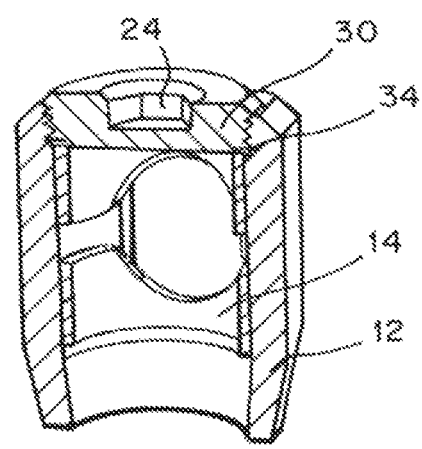

FIGS. 9A and 9B are cross-sectional views of the locking cap-tulip assembly including a groove 34 in the bottom of the threads 29 in the tulip 12 which produces an audible sound when the cap 22 is completely threaded into the tulip 12.

II. Methods of Use

The bone screw is positioned into the pedicle in a patient's spine using standard techniques for drilling a hole and placement of the screw.

For example, in a typical spinal fusion, first the entry site is decorticated using a burr and a high-speed drill or a rongeur. Next, a burr or awl is used to penetrate the dorsal cortex of the pedicle.

Then, a curved or straight pedicle probe is used to develop a path for the screw through the cancellous bone of the pedicle into the vertebral body. Advancement of the probe should be smooth and consistent. A sudden plunge suggests breaking out of the pedicle laterally; and an increase in resistance indicates abutment against the pedicle or vertebral body cortex.

Following cannulation, the pedicle sounding probe is placed into the pedicle that is then palpated from within to make sure there is not a medial, lateral, rostral, or caudal disruption in the cortex of the pedicles.

Preferably, audible sound should also be used to determine that there is bone at the bottom of the pilot hole verifying that penetration of the ventral cortex of the vertebral body has not occurred.

After pedicles have been probed, the surgeon can place Steinman pins or K-wires bilaterally or unilaterally into the pedicles to confirm the trajectory and entry site. Next, the surgeon may tap the pedicle screw path if non-self tapping screws are used.

Finally, the surgeon typically places permanent screws with the longest diameter that will not fracture the pedicle. The length of the screw is typically determined by measuring the length of the Steinman pin, K-wire, or pedicle probe from the pedicle entry site to a depth of 50-80% of the vertebral body. For example, the screws in the lumbar spine usually have a 4.5 to 7 mm diameter and a 35-50 mm length.

After pedicle screw placement, the transverse process and the lateral aspects of the facet joints are decorticated, and screws are connected to a rod. The rod(s) may need to be bent to conform to the proper curvature of the spine. Finally, screws are secured, and bone graft is then placed on the previously fusion bed.

Intraoperative Verification of the Screw Trajectory and Placement

After placement of the screws, the location of the screw may be verified. Lateral and an AP radiograph or fluoroscopic image does not guarantee accurate screw placement. Accuracy can be improved with a slightly oblique AP view—a pin located in the middle of the pedicle has a characteristic "target sign".

Direct AP views demonstrate the lateral to medial orientation of the screws. Excessive medial orientation of the screws seen on AP films raises the concern of medial penetration of the pedicle by the screw.

Lateral imaging is useful to view the depth of penetration into the vertebral body and sagittal angulation of the trajectory. Ventral screw penetration is usually between 50 and 80% of the AP diameter of the vertebral body; penetration greater than 80% of the vertebral body on lateral plain x-ray raises the concern of ventral penetration of the vertebral body cortex.

Modifications and variations of the locking caps and methods of use thereof will be obvious to those skilled in the art and are intended to come within the scope of the appended claims.

We claim:

1. A locking pedicle screw assembly comprising
    a cap, wherein the cap comprises a threaded portion, a swiveling upper saddle positioned at the bottom of the cap, and a retaining ring positioned above the swiveling saddle,
    a tulip, wherein the tulip comprises on an inner surface complementary threads to the threads on the cap and a groove,
    wherein the groove is in the tulip threads, and wherein the groove is configured for locking the retaining ring in the groove to align the cap within the tulip, and
    a bone screw, wherein the bone screw is configured to be secured to the tulip.

2. The locking pedicle screw assembly of claim 1 wherein the retaining ring is secured to a bottom surface of the cap.

3. The locking pedicle screw assembly of claim 1 further comprising a lower saddle for securing a spinal fusion rod.

4. The locking pedicle screw assembly of claim 3 wherein the retaining ring is positioned at the bottom of the threaded portion of the cap.

5. The locking pedicle screw assembly of claim 1, wherein the groove is below the complementary threads on the inner surface of the tulip.

6. The locking pedicle screw assembly of claim 1, wherein the groove is above the complementary threads on the inner surface of the tulip.

7. A method for securing a rod during spinal fusion surgery comprising implanting a bone screw assembly comprising
    a cap, wherein the cap comprises a threaded portion, a swiveling upper saddle positioned at the bottom of the cap, and a retaining ring positioned above the swiveling saddle,
    a tulip, wherein the tulip comprises on an inner surface complementary threads to the threads on the cap and a groove,
    wherein the groove is in the tulip threads, and wherein the groove is configured for locking the retaining ring into the groove to align the cap within the tulip, and
    a bone screw secured to the tulip,
    inserting the rod into the assembly, and
    rotating the cap until the retaining ring is in the groove.

8. The method of claim 7 wherein the locking screw cap retaining ring clicks into place in the groove.

9. The method of claim 7 wherein the retaining ring is secured to a bottom surface of the cap.

10. The method of claim 7 wherein the assembly further comprises a lower saddle for securing the rod.

11. The method of claim 10 wherein the retaining ring is positioned at the bottom of the threaded portion of the cap.

12. The method of claim 7, further comprising tightening the cap until it is locked.

* * * * *